(12) United States Patent
Hockaday et al.

(10) Patent No.: US 6,994,433 B2
(45) Date of Patent: Feb. 7, 2006

(54) ELECTROSTATIC FILTERED EYEWEAR

(75) Inventors: Robert G. Hockaday, Los Alamos, NM (US); Patrick S. Turner, Los Alamos, NM (US); Marc D. DeJohn, Los Alamos, NM (US); Carlos J. Navas, Santa Fe, NM (US); Heathcliff L. Vaz, Los Alamos, NM (US)

(73) Assignee: Energy Related Devices, Inc., Los Alamos, NM (US)

( * ) Notice: Subject to any disclaimer, the term of this patent is extended or adjusted under 35 U.S.C. 154(b) by 0 days.

(21) Appl. No.: 10/679,398

(22) Filed: Oct. 7, 2003

(65) Prior Publication Data

US 2004/0105070 A1 Jun. 3, 2004

Related U.S. Application Data

(60) Provisional application No. 60/416,271, filed on Oct. 7, 2002.

(51) Int. Cl.
*G02C 11/08* (2006.01)

(52) U.S. Cl. .............................. 351/62; 351/158; 2/436
(58) Field of Classification Search ................. 351/41, 351/44, 62, 158; 2/435–437
See application file for complete search history.

(56) References Cited

U.S. PATENT DOCUMENTS

| | | | |
|---|---|---|---|
| 2,379,493 A | 3/1945 | Morehouse | 128/201.23 |
| 4,176,410 A | 12/1979 | Matthias | 2/436 |
| 4,290,673 A | 9/1981 | Yamamoto | 351/62 |
| 4,689,838 A * | 9/1987 | Angermann et al. | 2/441 |
| 4,883,052 A * | 11/1989 | Weiss et al. | 128/205.27 |
| 5,115,804 A * | 5/1992 | Brookman | 128/201.22 |
| 5,186,165 A | 2/1993 | Swann | 128/201.28 |
| 5,428,411 A * | 6/1995 | Kopfer | 351/62 |
| 5,966,746 A * | 10/1999 | Reedy et al. | 2/436 |
| 6,119,689 A | 9/2000 | Korman | 128/205.29 |
| 6,158,429 A | 12/2000 | Gardner et al. | 128/201.25 |
| 6,318,369 B1 | 11/2001 | Gregory | 128/857 |
| 6,543,450 B1 * | 4/2003 | Flynn | 128/206.19 |
| 6,772,448 B1 * | 8/2004 | Hockaday et al. | 2/435 |
| 2004/0011363 A1 * | 1/2004 | Wiener et al. | 128/206.17 |

OTHER PUBLICATIONS

Perlman, M. M. and Reedyk, C. W.; *Production and Charge Delay of Film Electrets*; Journal of Electrostatics; 1968; 115(49) 86–89.

Kodera, Y. and Toyoda, T.; *Charge Stability of Annealed Electrets*; Charge Storage, Charge Transport, and Electrostatics; Edited by Wada, Perlman, and Kokada; Publication date unknown; pp. 113-117.

Fuhrmann, J. and Kurschner, J.; *Time dependent transient and intermittent contact electrification of polymers*; Journal of Electrostatics; 1981; 10: 115-120.

* cited by examiner

*Primary Examiner*—Huy Mai
(74) *Attorney, Agent, or Firm*—James C. Wray; Meera P. Narasimhan

(57) ABSTRACT

An eyewear has a gasket between the user and lenses that electrostatically filter the air flow of particulate while still permitting a gentle flow of air to maintain comfort to the wearer of the eyewear, and prevent fogging on the lenses. The electret filter material forms a perimeter around the eyes and lenses to remove, small to large particulates, from microns to millimeters. The filters can be formed with a choice of face contact gasket, baffles, coarse filters, and electret filter density. Baffles or coarse filters over the electret filters are used to protect the electret filter from damage from larger particles and transfer heat to the airflow.

94 Claims, 6 Drawing Sheets

A (10:1)

ELECTROSTATIC FILTERED EYEWEAR

This application claims the benefit of U.S. Provisional Application Ser. No. 60/416,271 filed Oct. 7, 2002.

BACKGROUND OF THE INVENTION

A major purpose of protective eyewear and glasses is to protect the eyes from dust and dirt and wind drying. When air flows around the lenses and past the eyes it carries with it dust, dirt, pollens, bacteria and particulates. In motorcycle goggles fine dirt and dust can filter through the airflow channels to the eye cavities and stick to the eyes of the user. In ski goggles fine particle snow can penetrate the filters. In safety goggles fine particulates can be entrained in the airflow through the vents and reach the eyes and surface of interior lens, irritating the eyes and obscuring vision. In all these eye-wear systems the main purpose is to block direct projectile impacts from colliding with the eyes of the user by using protective lenses while the goggles still must be ventilated to remove moisture and prevent fogging of the lenses.

The problem of fogging in sports goggles has been known for many years. In ski goggles this effect takes place when the interior of the lens reaches the dew point from the combination of cooling of the lens in contact with the cold outside air, and the flux of moisture into the interior air volume from the face. The fundamental concept to reduce fogging in goggles is to achieve a counter action to the effects of the heat removal through the lens and have the temperature of the air in the goggle be above the dew point. Attempts at making non-fogging goggles are quite numerous and typically rely on a variety of different techniques, but the most common is to have an open cell foam air filter along the perimeter gasket of the goggle. The cells of this foam are open enough to let air pass through while blocking the snow crystals. If the cells of the foam are very small or the foam is thick, it has a high resistance to airflow and can lead to insufficient airflow and fogging will occur in the goggles. If the foam is thin or the cells large in diameter the airflow is sufficient to prevent fogging but the finer ice crystals can pass through.

PRIOR ART

U.S. Pat. No. 2,379,493 Is an example of a patent of a breathing mask that protects the breathing passages and the eyes. This patent and other patents for full-face masks do not isolate the eyes and filter the air just for the eyes. They also use the breathing of the user to circulate the air.

U.S. Pat. No. 4,176,410 This is an example of several patents on sport goggles that use filters on the perimeter of the goggle to filter air into the eye lens volume and prevent fogging and the ingress of contaminates. This patent does not describe using electrets to filter the airflow or replaceable filters.

U.S. Pat. No. 4,290,673 A ski goggle with a heat-insulating interior space between the inner and outer lens plates using a water-repellent air-permeable filter. The filter is made out of ethylene tetrafluoride resin. This patent does not use the filter to ventilate the face lens volume and it does not identify the filter as an electret filter.

U.S. Pat. No. 4,883,052 A protective-breathing mask adapted to cover the mouth and nose of the wearer. Electret filters are used to filter the air to the wearer. It does teach that electret filters have an enhanced separation capacity particularly in relation to particles in the size range of 0.1 to 2 microns, and has a lower pressure drop with a comparable level of effectiveness compared to conventional particle filters. No mention of eyewear is made in this patent.

U.S. Pat. No. 5,186,165 Discloses head covering hood that uses and electrostatically charged filter to filter the incoming air of particles and protect the eyes. This patent does not describe using filters for just the eyes but covers the entire head and air is removed by the breathing of the wearer. Full head hoods can be cumbersome and insulate the user, thus being hot and uncomfortable. Our invention creates an airflow and filtered environment for just the eyes.

U.S. Pat. No. 6,119,689 Disclosed an electrostatic filter used as a personal filter unit. It uses the electrostatic filter in conjunction with conventional filters. This patent does not describe filtering the air just for the eyes and breathing moves the airflow.

U.S. Pat. No. 6,158,429 Disclosed a hood respirator using electrets in filtering air to protect the eyes. It also describes protecting the surface media with thin nylon screen mesh, and using air flow deflectors of soft plastic material to form a channel to direct air over the lenses to prevent fogging. This patent does not describe filtering the air just for the eyes and breathing moves the airflow.

U.S. Pat. No. 6,318,369 B1 Eye, ear, and respiration protective apparatus. This patent uses an air filter to filter air into the respiratory tract and describes an eye protection attachment. This patent does not describe filtering the air to the eyes or using electrets in the eye filters.

REFERENCES

1. Martin Pearlman and Cornelis Reedyk, Production and Charge Decay of Film Electrets, J. Electrostatics, 115, 49 (1968).
2. Yoichi, Kodera, and Tetsuo Toyoda, Charge Stability of Annealed Electrets, Charge Storage, Charge Transport and Electrostatics with their Applications, Edited by Y. Wada, M. Pearlman and H. Kokado, pp 113–117.
3. J. Fuhrmann and J. Kurschner, Time Dependent Transient and Intermittent Contact Electrification of Polymers, J. Electrostatics, 10 (1981) 115–120.

SUMMARY OF THE INVENTION

There are six typical mechanisms in the goggles that can be used to remove moisture from the eye lens volume: natural convection, ram air circulation, airflow pumping, diffusion, absorption, and condensation. Our pending patent (U.S. 60/339,394 Non Fogging Goggles) and references contained therein summarize these techniques, which is incorporated herein by reference in its entirety. This pending patent discloses thermally conductive face contact materials in the face contact gasket to conduct heat from the cheek and nose body contact points to the incoming air into the face lens volume while impeding the transfer of moisture from the body contact areas. This is a combination of a more thermally conductive face foam gasket with a moisture impermeable barrier on the interior facing side, coupled to thermally conductive and heat exchanging surfaces of thermally conductive honeycomb air inlets, and/or grooved or finned surfaces on the interior on the goggle frame.

Enhancing the heat transfer to baffles and filters can be accomplished by several refinements of the eyewear, such as:

Bonding filter to the frame or in the air vent inserts.

Making the baffles tapered toward the face, with the thickest portion near the face (optimizing the heat transfer and conduction for a given mass).

Ensuring maximum thermal contact between the filters and baffles with the eyewear frame.

Building the eyewear face gasket, frame and filter materials to have a high thermal conductivity.

Thermally insulating the outer baffles and outer surfaces of the frame to avoid heat losses to the outside air.

The face gasket features moving water, that is condensed on the interior or surface of the gasket, to the outer perimeter by wicking. The face gasket has the two functions of moving water away from the surface of the skin outside the face-lens volume and transferring heat to the goggle frame and heat transfer surface, while it still must perform the essential function of sealing the goggle to the face to prevent snow from entering the face-lens space. In our pending patent, U.S. 60/339,394 Non Fogging Goggles, air flow inlet and outlet channels are created that have low impedance to flow while maximizing their heat transfer and snow blocking function to create a convection air flow regardless of outside conditions. The heat transfer feature is essentially trying to optimize the chimney effect. The lighter warm air removes moisture from the lens-face volume while maintaining the snow blocking function. The embodiment is a thermally conductive honeycomb, chevrons, open cell foams, fibers, screens or slotted inlets and outlets. The effective diameter and length of the channel are sized to minimize flow drag and maximize heat transfer while maintaining dust or snow blocking. With a high enough airflow our research has shown that goggles in almost all cold weather conditions will remain clear. We have found, by testing commercially available goggles, that the typical snow filter foam has a cell size and thickness that presents a very high resistance to natural convection in goggles. The critical scaling parameter for airflow through these small air inlets (laminar flow) is that airflow resistance per unit area is proportional to the length of the channels and inversely proportional to the square of the aperture size.

Another feature is to form an upper air outlet channel with low flow impedance, block snow ingress, move liquid water away from the face-lens space, and are shielded from airflow effects outside the goggle. The upper air vent does not significantly need to have heat transfer from the body to clear the lens. It does help to avoid condensation in the top exit and makes a small contribution to the chimney effect. The two critical functions of the upper outlet is to let the moisture laden warm air vent out to the atmosphere and prevent, dust, snow, or liquid water from getting back into the goggle. A condensed water channel to wick or draw condensed water can be created in the upper vents to move water off the top of the goggles.

We have found that the disclosures in the aforementioned pending patent, while preventing fogging of the goggles, cannot adequately block all particles from entering the goggle and irritating the user's eyes. Thus, some improvements are needed, which the present invention addresses.

By using electrostatic filtration the smaller ice crystals or particles can be attracted to the filter effectively increasing the filtration capacity without increasing the airflow resistance of the filter. When the air is very cold the ice particles can bounce off the open cell foams and not condense. Therefore, the electrostatic filter can hold the ice particles to the surface of the electret fibers until they either melt, or conglomerate with other particles and improve the airflow characteristics of the goggle while still obtaining a high degree of particulate filtration.

Electret filtration uses materials such as polypropylene, polystyrene, polycarbonate, and FEP TEFLON, poylvinylidenefluoride ($PVF_2$) that, in intermittent contact with a strong electric field or corona discharge, become charged and thereby have a permanent electric field or a resonance time in the order of years[1]. When the particles of micron and sub-micron dimensions are in the presence of the electric field of the electret, due to the intrinsic charge of small particles, they will be attracted to the surface of the electret and stick. While most of the micron dimension and smaller particles typically will be charged, the uncharged particles can be charged and accelerated with strong electric fields. High voltage corona discharges from metal points and small diameter wires, sharp plate edges, or plates can be used to charge the dust and allow it to be attracted to filter surfaces. The dust particles are attracted to the surrounding surfaces. Once they are on the surface of the electret they can conglomerate with other particles and effectively are removed from the air stream. Long lifetime charged electret filtration products for air filters have been used for many years to remove airborne dust particle with enhanced performance over the range of 0.1 to 2 microns micron diameter particles (U.S. Pat. No. 4,883,052).

To optimize electret air filter systems there are charged air channels of plastic or fibers of charged plastic that act on the particles over a distance of flow. If viscosity effects are ignored the first order maximum air flow rate for an electrostatic filter is proportional to the depth of the filter, the square root of the particle charge, electric field strength, the square root of the inverse of the filter pore width, and particle mass. The laminar airflow drag energy per unit of airflow through a filter is roughly proportional to the thickness of the filter and average flow velocity. It is also inversely proportional to the square of the pore diameter in the filter. Thus, to obtain good filtering performance the electrostatic filter should have high thickness, large pores, high electric field, and low airflow rate. Not all particles will be charged or be of small enough mass to be filtered by the electret filter, so coarse filters that protect the electret filter from large particles can be used. The filter pores can be sized small enough to also mechanically block the larger particles. Electrostatic filters typically demonstrate an advantage over conventional filters in efficiently removing particles between 0.1 and 2 microns in diameter (U.S. Pat. No. 4,883,052).

To obtain a high figure of merit for a filter, low energy expenditure and high maximum filter velocity is desirable. Thus, it is best to minimize the flow velocity through the filter, by having the largest possible area for the filter with the largest possible pore aperture dimension in the pores of the filter while still having sufficient depth to attract the particles. Folded and large pore filters, and large area filters are better than thin flat small pore filters. In designing the filters for eye wear filtration, they should maximize the cross-sectional area to the flow and depth. The filters may fill much of the perimeter area between the lens and the face to maximize the flow area. Filters can consist of charged honeycomb or corrugated electret structures, open cell charged electret foams, sheets of electrets, molded parts, a liner around the perimeter of the lenses, or loosely packed fibrous electrets.

By combining efficient electret filtration with thermal heat transfer in the frame of the goggle, more dust-free and non-fogging goggles or glasses can be achieved. In this invention by forming the outer baffles, filters and outer surfaces of the frame with low thermal conductivity materials, and by forming the perimeter of the goggles, forming the outer baffles, filters and outer surfaces of the frame with low thermal conductivity materials, the perimeter of the goggles reduces heat losses. Forming the interior baffles, filter and inner frame surfaces with thermally conductive materials increases the heat transfer from the face to incoming air and inner lens. This reduces fogging by increasing the temperature of the inner lens and increases the moisture removal rate. Thus, the combined efficient electret filtration and thermal transfer leads to an improved dust exclusion and non-fogging eyewear.

These and further and other objects and features of the invention are apparent in the disclosure, which includes the above and ongoing written specification, with the drawings and the claims.

DETAILED DESCRIPTION OF THE PREFERRED EMBODIMENTS

Figure 1:
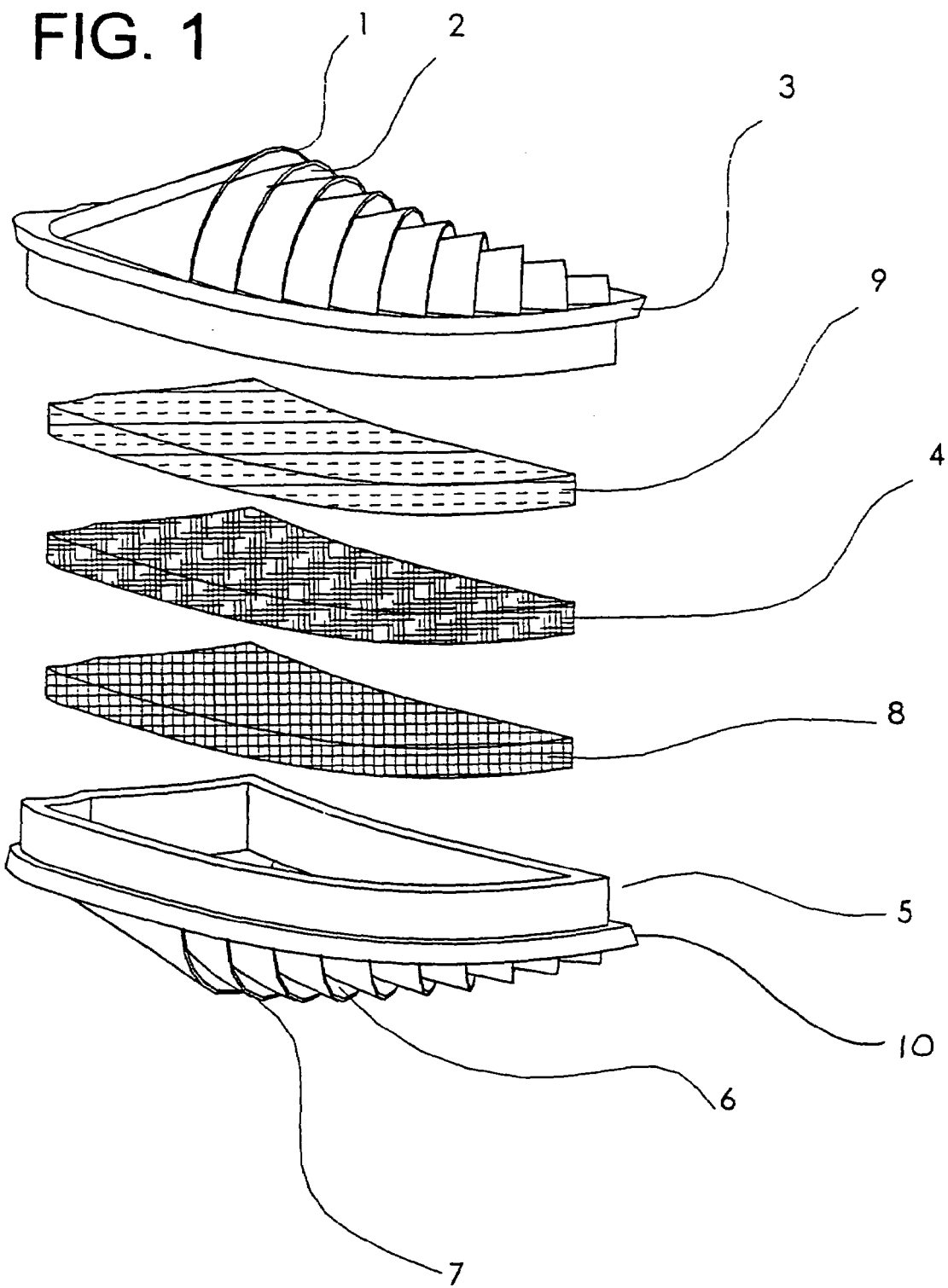
FIG. 1. Shows an exploded view of a filter insert.

Shown in FIG. 1 is an exploded view of a goggle air vent insert with electret filter. The electret filter insert is formed by molding urethane rubber (Stevens Urethane, Nine Sulivan Road, Holyoke, Mass. 01040-2800), or silicone rubber (GE Silicones of General Electric Company, Waterford, N.Y., 12188), 1,3,5,7 that has been doped with $Al_2O_3$, SiC, MgO, $SnO_2$, +Mg, graphite, or Al particles around an electret filter 4 such as Filtete™, 3M Construction and Home Improvement Markets Division, Box 330533, St. Paul, Minn. 55133-3053. The baffles interior 1, and exterior 7 can be designed to optimize the heat transfer by thickening the baffles near the goggle frame thermal contacts 3, 5 and forming fins in the baffles. The filter inserts 1, 5 can also be formed out of metals such as Mg or Al for their properties of high thermal conductivity and are lightweight. One of the design variations is to form the filter insert with a high conductivity interior material baffle 2 or screen 9 and have the exterior baffle 7 or screens 8 made with low thermal conductivity material such as foamed urethane or foamed silicone rubber. The baffles on the interior side 1 can be coated or incorporated with a carbon black for higher emissivity heat transfer and to avoid light reflection off the interior of the goggles. The objective is to maximize the heat transfer to the airflow while still insulating the interior space and goggle frame from the cold air outside the goggles. The filter insert 1, 5 is formed to fit into holes in the urethane rubber frame of the goggles, shown in FIG. 4. A lip 3 and 10 is formed to allow the insert 1, 7 to frame the insert hole in the goggle. Baffled flow channels 2, 6 are formed to have a low resistance to air flow and heat transfer to the gas flowing through the air while still being a barrier to large dust particles and snow. The filter inserts 1, 5 can be formed as two components and glued (Acrylic Adhesive DP 8005, 3M Adhesives, Division, St. Paul, Minn. 55144-1000), or snapped together with ratchets to clamp the electret filter 4 and the adjacent non-electret filter. Aluminum wire screen 9, and plastic fiberglass mesh 8, are inserted between the baffles 1, 5. Other versions can have the rubber baffles 2, 7 molded around the electret filters. The electret filter can be formed by tearing up already charged polypropylene plastic film into thin fibers, or spinning polypropylene fibers and then subjecting the polypropylene fibers to a high voltage electric discharge. Other suitable plastics to form long lifetime electrets are polycarbonate plastic polyvinylidene-fluoride $PVF_2$ and polystyrene[1,2,3]. The charged electret fibers can be formed into a felt or woven fabric. The polypropylene can also be formed into an airflow channel structure such as a honeycomb. Other suitable structures are an array of parallel sheets of electret separated by corrugated electret sheets or bundles of electret tubes partially fused together.

Figure 2:
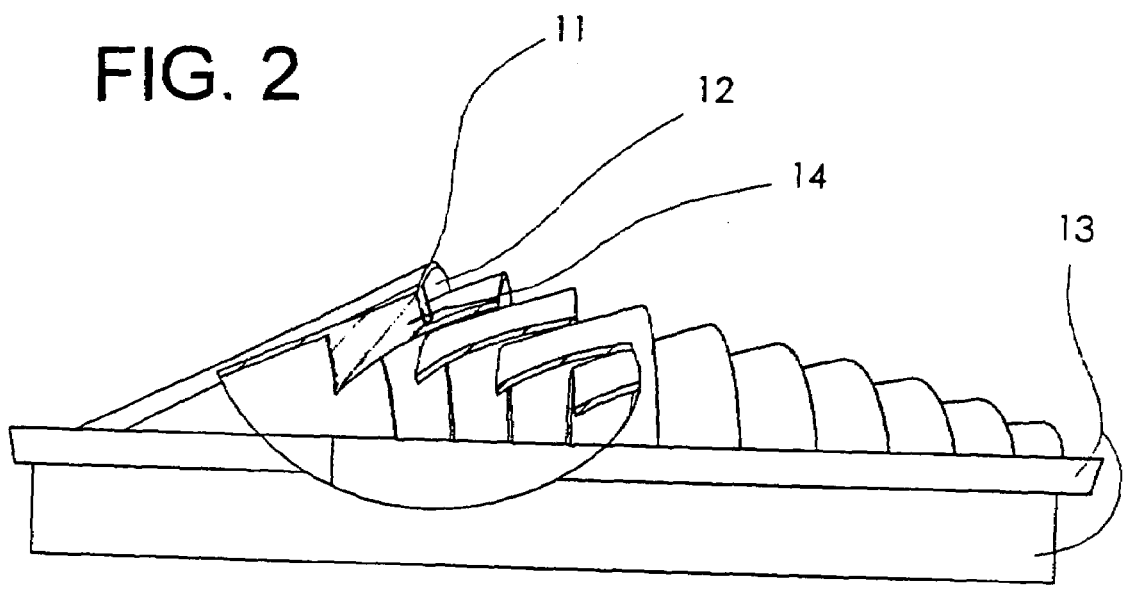
FIG. 2. Cut away view of baffled air vent cover.

FIG. 2 shows a side view of just one side of the insert with a cutout of the baffles 11. The urethane or silicone rubber doped with $Al_2O_3$, SiC, MgO, $SnO_2$, Mg, graphite, or Al particles is injection molded. Airflow channels 12 are formed. These airflow channels act as baffles to deflect or block particles in the airflow outside the goggles. They also act as heat transfer surfaces from the thermal coupling to the goggle frame along the attachment area 13. The airflow channels of the baffles can have a variety of shapes to transfer heat efficiently to the flow and minimize airflow resistance, such as honeycombs and slots with fins or grooves in them 14. The baffles also act as flow directors to be able to use ram air to enhance, be neutral, or counter to the effects of the wearer moving through the air. In most of the cases the air flow ducts should be arranged with respect to the airflow to result in comfortable airflow due to convection when the wearer is stationary and a slightly higher flow rate when the wearer is moving. The deflectors should be directed away from the eyes and across the lenses to maximize the anti-fogging and eye comfort.

Figure 3:
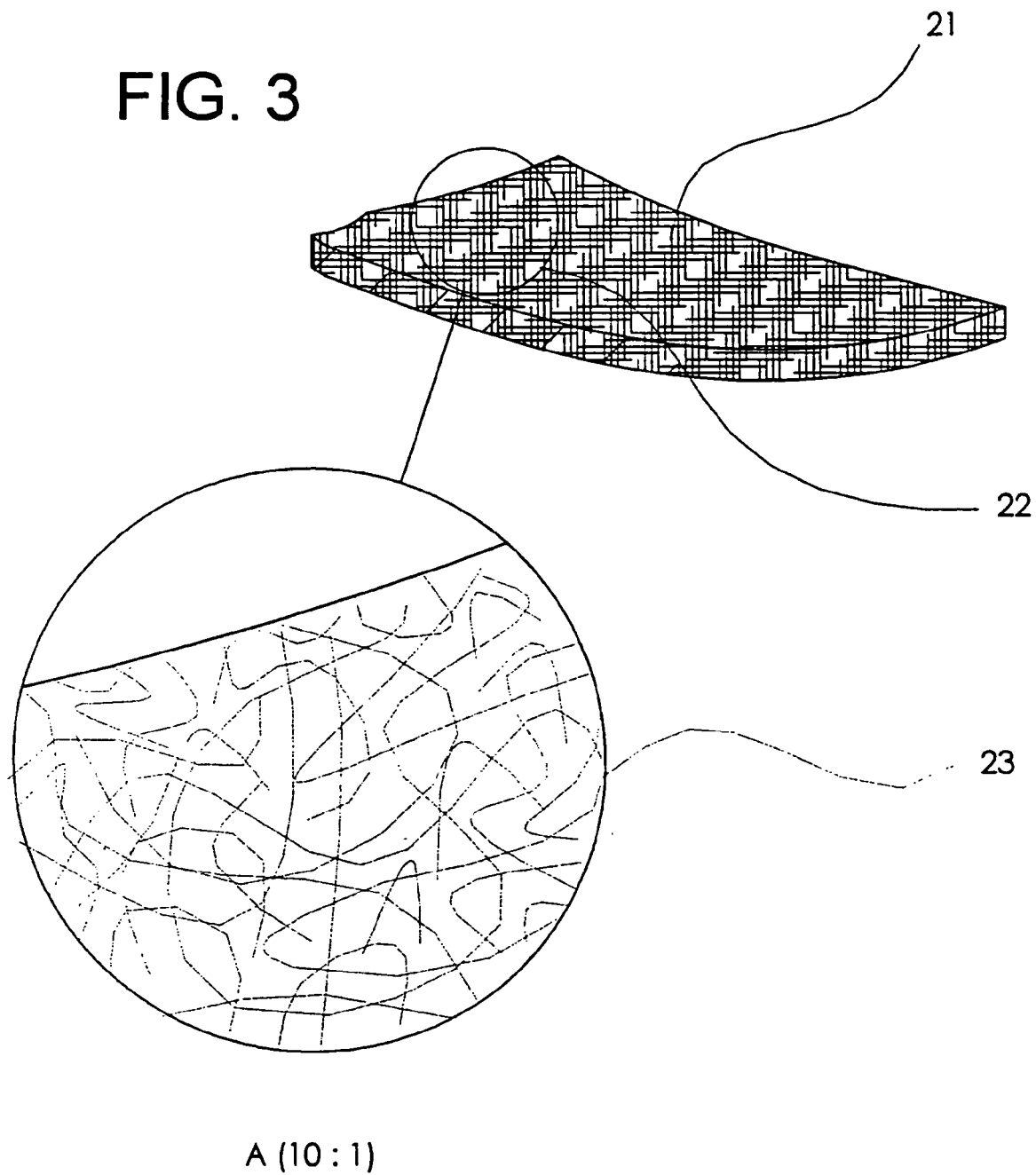
FIG. 3. Electret filter element and enlarged view of filter.

In FIG. 3, the electret filter is shown with an enlarged view 22 of the electret fibers. The electret filter 21 shown here is a fibrous polypropylene 23 that can be obtained from 3M corporation (Filtrete™, 3M Construction and Home Improvement Markets Division, Box 33053, St. Paul, Minn. 55133-3053). Other suitable electret materials are polycarbonate, $PVF_2$ and polystyrene. Subjecting the plastic fibers to a DC or AC corona electrical discharge can charge the electret. The electret filter can also be sandwiched with a backing material such as a plastic coated fiberglass mesh to make it more mechanically robust and act as a conventional filter. In other embodiments of this invention the electret filter alone or with backing materials can be glued (Acrylic Adhesive DP 8005, 3M Adhesives, Division, St. Paul, Minn. 55144-1000), to cover the apertures of the goggle.

Figure 4:
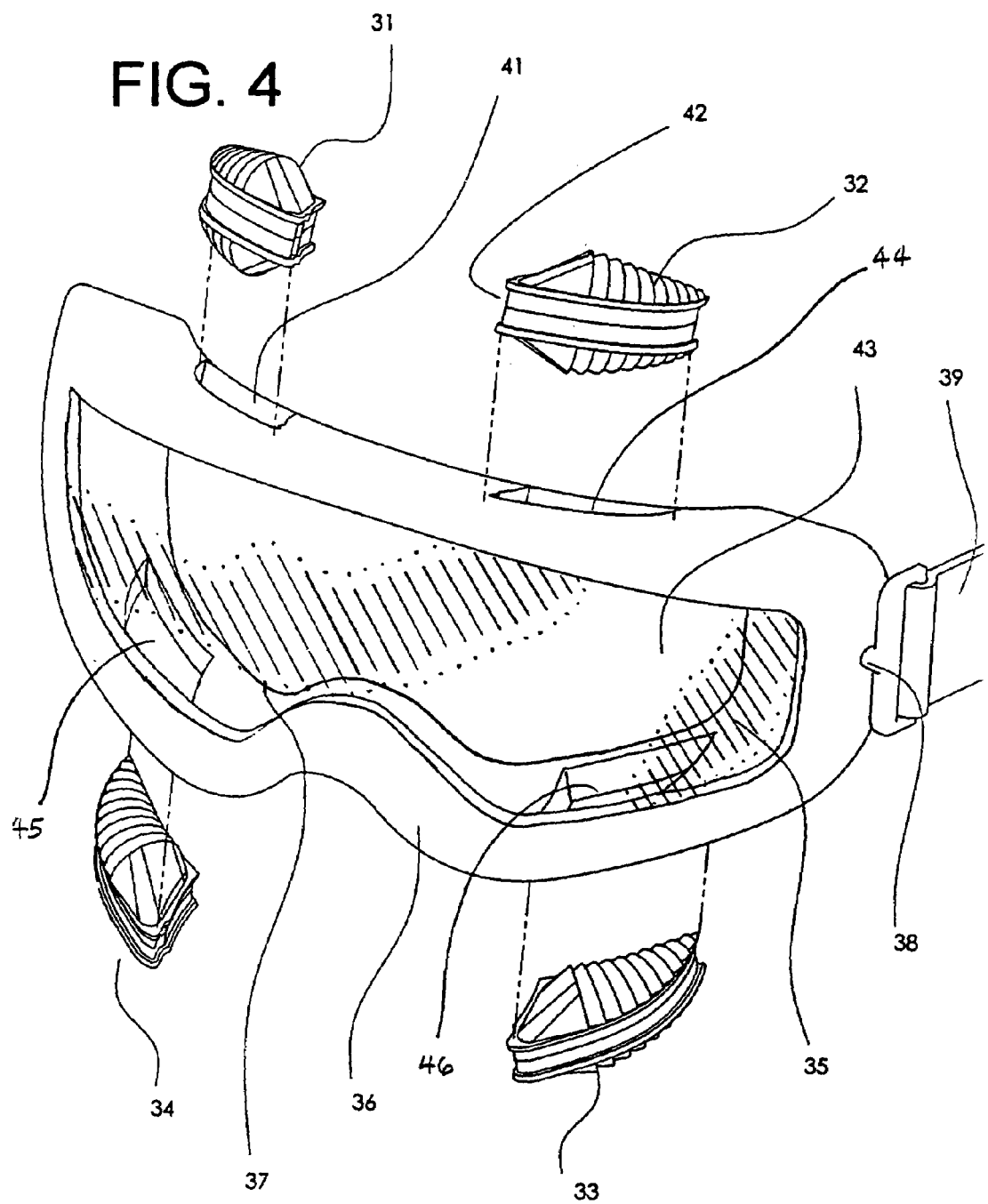
FIG. 4. Baffles and electret filter insert placed in goggles.

In FIG. 4 the filter inserts are shown where they can be inserted into the frame of the goggle 43. The goggle frame 36 makes sealing contact with the face of the wearer with a soft wicking gasket or foam gasket 37. If the electret filter inserts are made of soft pliable rubber, or the goggle frame is pliable, the inserts can be pressed into the frame holes 41,44,45,46 of the goggle and framing the holes with inserts 31, 32, 33, 34. The upper right hand 31, upper left hand 32, lower left hand 33, and lower right hand 34 inserts are shown as unique shaped inserts. Possible designs are to make the filter inserts 31, 32, 33, 34 symmetrical so one-filter insert fits any of the frame holes 42. The goggle inserts 31, 32, 33, 34 are placed in the frame of the goggle; the goggle 43 are worn over the eyes and the strap 39 holds the goggles in place on the head of the wearer. The strap is attached to the goggle through a bracket 38. The goggle typically for skiing has two clear plastic lenses 35. In safety goggles the lens 35 is a single lens. The contact compression of the goggle 43 on the face gasket 37 with the face of the wearer can be adjusted by slipping the strap 39 through the bracket 38.

Figure 5:
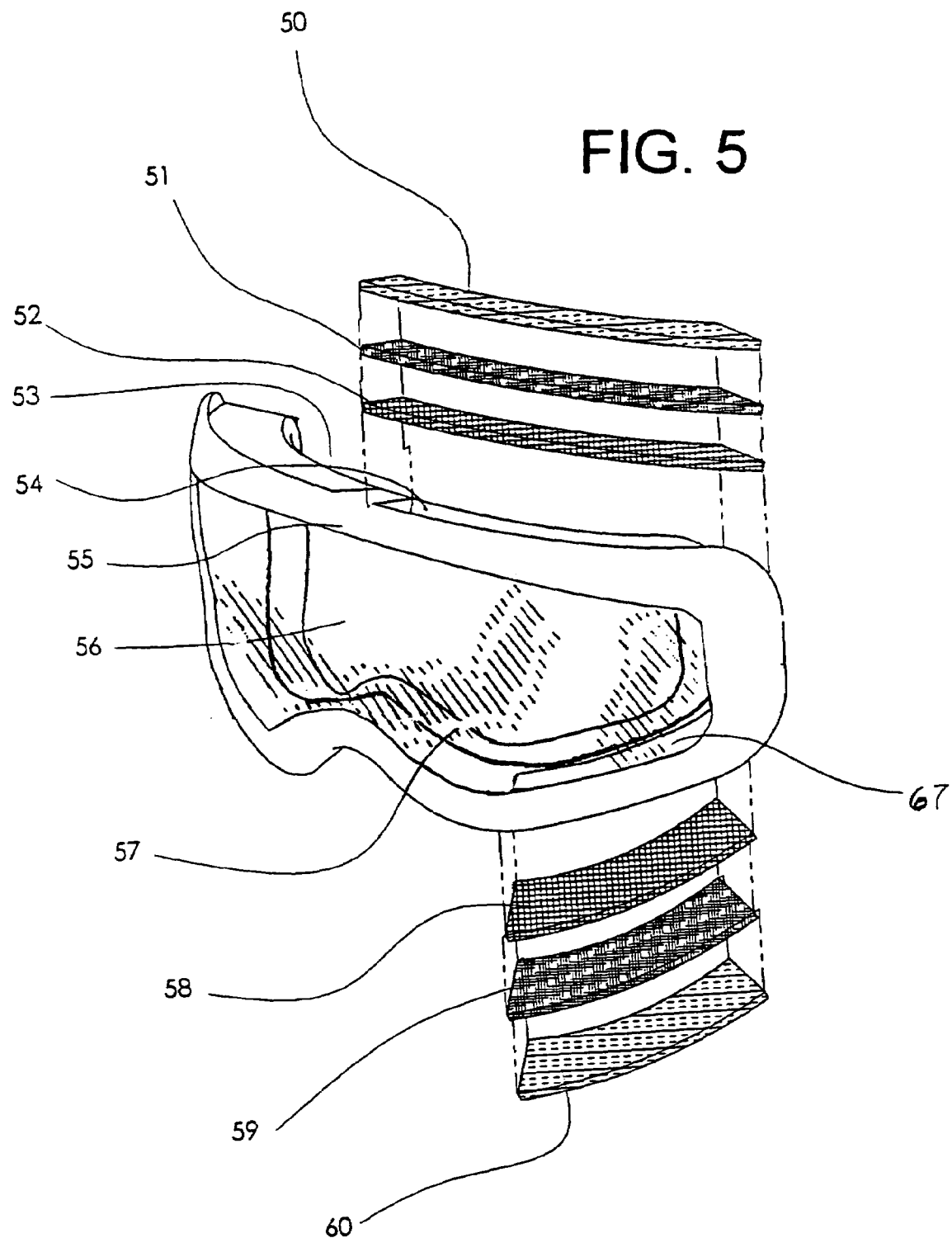
FIG. 5. Layered filter exploded view with left-hand side of goggle.

FIG. 5 shows the embodiment of the goggle with cover screens and electret filter bonded onto the ports of the goggle. Only filters for the right hand side are shown in the exploded view. In this construction a plastic coated fiberglass mesh 50 (Hanover wire cloth, Star Brand Screening, Division of CCX, Inc., Hanover Pa. 17331) is placed on top of the polypropylene fine fiber filter 51 on top of the aluminum coarse mesh 52 (Delker Corporation, 14 Commercial St., Branford Conn., 06405). All three layers are attached, bonded, or glued to the urethane goggle frame 55 covering and filling the ventilation slot 54. The goggle frame holds the double lenses 56 and the face contact gasket 53, 57. The face contact gasket 57, 52 shown is glued to the frame of the goggle 55 with acrylic adhesive. On the under side of the goggle frame 55 the air intake filters are shown. The aluminum, graphite, or magnesium mesh 58 is placed in first, a polypropylene electret fiber filter 59 and then a fiberglass reinforced urethane plastic coated mesh 60. The interior mesh 58 can be coated with a blackening coating such as carbon black loaded paint to give it a high emissivity and light absorption properties for heat transfer and to avoid light reflection on the interior of the goggles. The filter assembly 58, 59, 60 is glued with acrylic adhesive over the lower ventilation slot 67 in the frame of the goggle 55.

Figure 6:
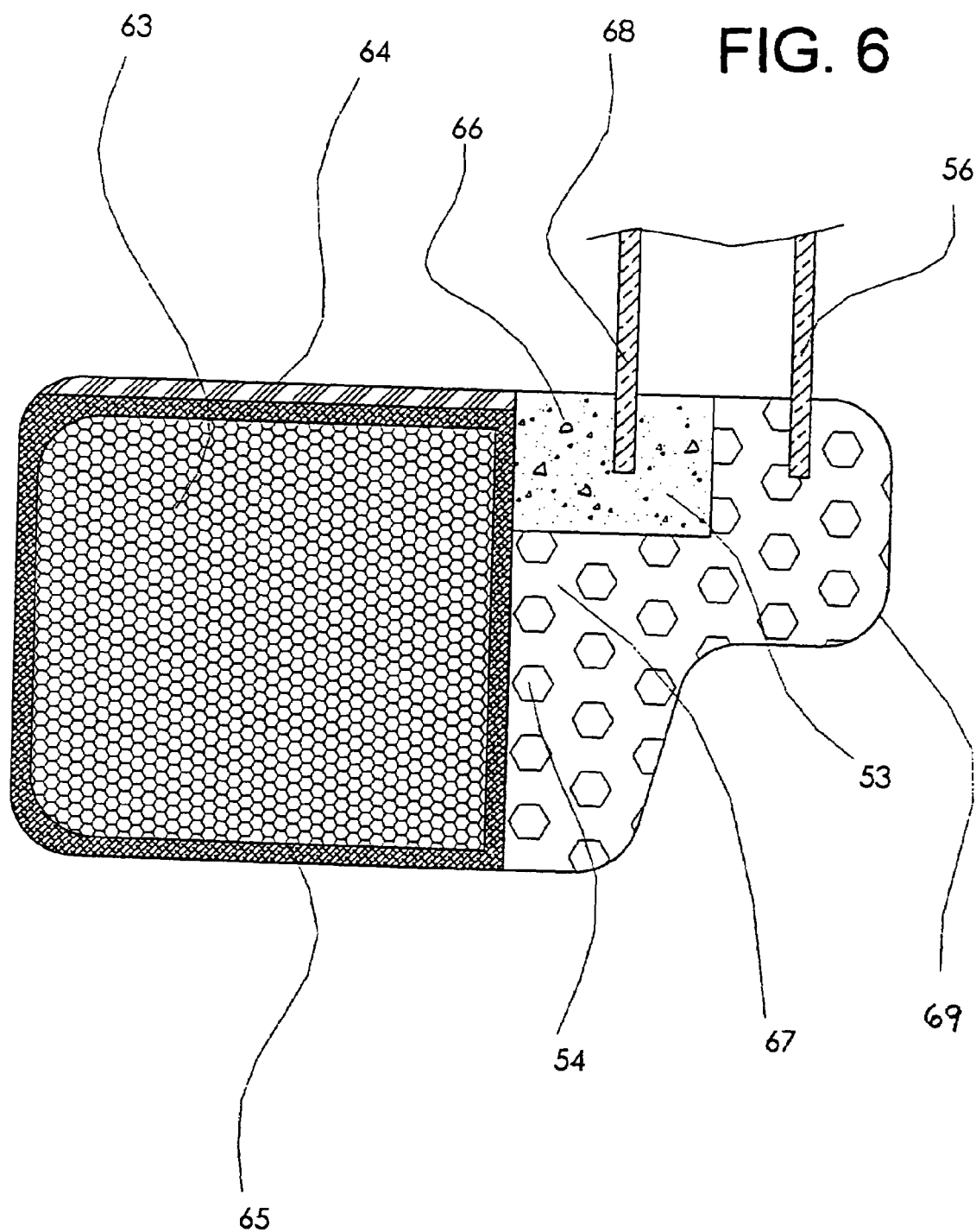
FIG. 6. Cross-sectional view through the face contact gasket and frame.

In FIG. 6 an enlarged view of the frame and face gasket are shown. The goggle frame 69 can be constructed of an interior surface that is made of urethane rubber 53 filled with a thermally conductive powder such as aluminum, magnesium, graphite, $Al_2O_3$, SiC, MgO, $SnO_2$, or graphite fibers 66 in thermal contact with the inner lens 68. The exterior of the goggle urethane rubber 67 is filled with bubbles of air, argon, nitrogen, $SF_6$, or glass micro-balloons 54 (Wrigley Fibers, F. H. Wrigley Ltd., Williton Industrial Estate, Williton, Somerset, TA4 4RF, UK.), to give it thermal insulation properties. Open cell urethane foam 63 sealed on the interior with silicone rubber 64 (GE Silicones of General Electric Company, Waterford, N.Y., 12188), and has a silk or Cool Max™ polyester (Intex Corporation, 1031 Summit Ave., Greensboro, N.C. 27405), wicking gasket 65 that is open to the perimeter to wick water to the perimeter, and sealed from wicking of water on the interior side with a thin film of silicone sealant 64.

While this invention has been described with reference to specific embodiments, modifications and variations of the invention may be constructed without departing from the scope of the invention, which is defined in the following claims and the drawings.

We claim:

1. An eyewear device comprising a frame, lens on the frame, and a filter disposed between the lens and a user's face for filtering air in an air volume in the eyewear, wherein the filter is an electrostatic filter.

2. The device of claim 1, wherein the filter enables heat transfer for transferring heat into an airflow from thermal heat of the wearer's face.

3. The device of claim 1, wherein the filter is selected from a group consisting of screens, wires, fibers, open cell foams, and combinations thereof.

4. The device of claim 1, further comprising a channel disposed adjacent to the filter.

5. The device of claim 4, wherein the channel is selected from the group consisting of baffles, fins, honeycombs, molded parts, and combinations thereof.

6. The device of claim 1, wherein the electrostatic filter is selected from a group consisting of baffles, fins, parallel planes, sheets, tube bundles, corrugated sheets, honeycombs, molded parts, corona discharge points, charged plates, charged wires, and combinations thereof.

7. The device of claim 1, wherein the electrostatic filter is an electret.

8. The device of claim 7, wherein the electret is selected from the group consisting of plastic, polypropylene, polycarbonate, FEP Teflon, poylvinylidenefluoride, $PVF_2$, and combinations thereof.

9. The device of claim 1, further comprising baffles disposed adjacent to the filter.

10. The device of claim 9, wherein the baffles comprise heat transfer enhancers.

11. The device of claim 10, wherein the enhancers are selected from the group consisting of surface coatings, fillers, tapers, fins, convolutions, grooves, bumps, and combinations thereof.

12. The device of claim 10, wherein the enhancers are selected from a group consisting of $Al_2O_3$, SiC, MgO, $SnO_2$, Mg, graphite, Al, high emissivity coatings, carbon black coatings, and combinations thereof.

13. The device of claim 1, further comprising an insert for receiving the filter.

14. The device of claim 13, wherein the insert is selected from the group consisting of non-electrostatic filters, screens, wires, fibers, open cell foams, baffles, honeycombs, and combinations thereof.

15. The device of claim 1, wherein the filter is replaceable and removably disposed on the frame of the eyewear.

16. The device of claim 1, further comprising a module for the filter.

17. The device of claim 16, wherein the module is replaceable and removably disposed on the frame of the eyewear.

18. The device of claim 17, wherein the module is of material selected from a group consisting of molded plastic, metal, rubber, and combinations thereof.

19. The device of claim 18, wherein the filter is removably incorporated in the module.

20. The device of claim 1, wherein the lens comprises interior-facing portions and exterior-facing portions, wherein the interior-facing portions have higher thermal conductivity and extensive contact areas with air than the exterior-facing portions.

21. The device of claim 1, wherein the frame comprises an exterior having low thermal conductivity.

22. The device of claim 21, wherein the exterior comprises low thermal conductivity materials.

23. The device of claim 21, wherein the exterior comprises voids, bubbles, gas bubbles, and combinations thereof.

24. The device of claim 21, wherein the exterior comprises a surface layer.

25. The device of claim 24, wherein the surface layer is a low thermal conductivity layer.

26. The device of claim 21, wherein the frame comprises an interior having high thermal conductivity.

27. The device of claim 26, wherein the interior comprises high thermal conductive metal particles.

28. The device of claim 26, wherein the interior comprises high thermal conductivity fibers.

29. The device of claim 26, wherein the interior comprises high thermal conductivity particles incorporated therein.

30. The device of claim 26, wherein the interior comprises high thermal conductivity flakes.

31. The device of claim 26, wherein the frame is of plastic material.

32. The device of claim 26, wherein the frame is a rubber molded frame.

33. The device of claim 1, wherein the layer is of plastic material.

34. The device of claim 33, wherein the layer is of molded rubber.

35. The device of claim 34, further comprising a low thermal conductivity layer on the eyewear.

36. The device of claim 33, wherein the layer comprises gas bubbles.

37. The device of claim 36, wherein the bubbles are selected from the group consisting of air, argon, nitrogen, $SF_6$, glass micro-balloons, and combinations thereof.

38. The device of claim 36, wherein the layer is a surface layer on the frame.

39. The device of claim 33, wherein the layer is of material with low thermal conductivity.

40. The device of claim 33, wherein the layer is disposed on an exterior of the frame.

41. The device of claim 33, further comprising a high thermal conductivity layer on the eyewear.

42. The device of claim 41, wherein the layer comprises metal particles.

43. The device of claim 42, wherein the metal particles are selected from a group consisting of $Al_2O_3$, SiC, MgO, $SnO_2$, Mg, Al, graphite, and combinations thereof.

44. The device of claim 42, wherein the layer comprises high thermal conductivity fibers.

45. The device of claim 44, wherein the fibers are selected from the group consisting of SiC, Al, Mg, C, and combinations thereof.

46. The device of claim 1, wherein the eyewear comprises heat transfer portions in thermal contact with the user's face for transferring heat into an air flow from the face, and wherein an interior facing portion has high thermal conductivity and an exterior facing portion has a low thermal conductivity.

47. The device of claim 46, wherein the portions are disposed on areas of the eyewear selected from the group consisting of the frame, the lens, the filter, and combinations thereof.

48. A dust-proof non-fogging eyewear comprising a frame, lenses on the frame, and a filter gasket disposed between a user's face and the lenses for electrostatically filtering air flow of particulate but permitting a gentle flow of air to maintain comfort to a user and preventing fogging on the lenses.

49. The eyewear of claim 48, wherein the filter comprises electret filter material forming a perimeter around a user's eyes and the lenses for removing particulates from the air flow.

50. The eyewear of claim 49, further comprising inserts for the filter.

51. The eyewear of claim 50, wherein the inserts are removable and replaceable.

52. The eyewear of claim 51, wherein the inserts are selected from the group consisting of face contact gaskets, baffles, coarse filters, electret filters, and combinations thereof.

53. A filter and eyewear apparatus comprising an electrostatic filter mountable between lens of the eyewear and a user's face for filtering air in an air volume in the eyewear.

54. The apparatus of claim 53, wherein the filter enables heat transfer for transferring heat into an airflow from thermal heat of the wearer's face.

55. The apparatus of claim 53, wherein the filter is selected from a group consisting of screens, wires, fibers, open cell foams, and combinations thereof.

56. The apparatus of claim 53, wherein the electrostatic filter is selected from a group consisting of baffles, fins, parallel planes, sheets, tube bundles, corrugated sheets, honeycombs, molded parts, corona discharge points, charged plates, charged wires, and combinations thereof.

57. The apparatus of claim 53, wherein the electrostatic filter is an electret.

58. The apparatus of claim 57, wherein the electret is selected from the group consisting of plastic, polypropylene, polycarbonate, FEP Teflon, poylvinylidenefluoride, $PVF_2$, and combinations thereof.

59. The apparatus of claim 53, further comprising baffles disposed adjacent to the filter.

60. The apparatus of claim 59, wherein the baffles comprise heat transfer enhancers.

61. The apparatus of claim 60, wherein the enhancers are selected from the group consisting of surface coatings, fillers, tapers, fins, convolutions, grooves, bumps, and combinations thereof.

62. The apparatus of claim 60, wherein the enhancers are selected from a group consisting of $Al_2O_3$, SiC, MgO, $SnO_2$, Mg, graphite, Al, high emissivity coatings, carbon black coatings, and combinations thereof.

63. The apparatus of claim 53, further comprising an insert for receiving the filter.

64. The apparatus of claim 63, wherein the insert is selected from the group consisting of non-electrostatic filters, screens, wires, fibers, open cell foams, baffles, honeycombs, and combinations thereof.

65. The apparatus of claim 53, wherein the filter is replaceable and removably disposed.

66. The apparatus of claim 53, further comprising a module for the filter.

67. The apparatus of claim 66, wherein the module is replaceable and removably disposed on the eyewear.

68. The apparatus of claim 67, wherein the module is of material selected from a group consisting of molded plastic, metal, rubber, and combinations thereof.

69. The apparatus of claim 68, wherein the filter is removably incorporated in the module.

70. The apparatus of claim 53, further comprising at least one lens on the eyewear.

71. The apparatus of claim 70, wherein the at least one lens comprises interior-facing portions and exterior-facing portions, wherein the interior-facing portions have higher thermal conductivity and extensive contact areas with air than the exterior-facing portions.

72. The apparatus of claim 53, further comprising a low thermal conductivity layer on the eyewear.

73. The apparatus of claim 72, wherein the layer comprises gas bubbles.

74. The apparatus of claim 73, wherein the bubbles are selected from the group consisting of air, argon, nitrogen, $SF_6$, glass micro-balloons, and combinations thereof.

75. The apparatus of claim 72, wherein the layer is of material with low thermal conductivity.

76. The apparatus of claim 53, further comprising a high thermal conductivity layer on the eyewear.

77. The apparatus of claim 76, wherein the layer comprises metal particles.

78. The apparatus of claim 77, wherein the metal particles are selected from a group consisting of $Al_2O_3$, SiC, MgO, $SnO_2$, Mg, Al, graphite, and combinations thereof.

79. The apparatus of claim 76, wherein the layer comprises high thermal conductivity fibers.

80. The apparatus of claim 79, wherein the fibers are selected from the group consisting of SiC, Al, Mg, C, and combinations thereof.

81. The apparatus of claim 53, wherein the eyewear comprises heat transfer portions in thermal contact with the user's face for transferring heat into an air flow from the face, and wherein an interior facing portion has high thermal conductivity and an exterior facing portion has a low thermal conductivity.

82. A filter for eyewear comprising an electrostatic filter disposed between a user's face and lens of the eyewear for electrostatically filtering air in an air volume in the eyewear.

83. The filter of claim 82, wherein the filter comprises electret filter material forming a perimeter around a user's eyes and the eyewear for removing particulates from the air flow.

84. The filter of claim 82, wherein the filter is selected from a group consisting of screens, wires, fibers, open cell foams, and combinations thereof.

85. The filter of claim 82, wherein the filter is selected from a group consisting of baffles, fins, parallel planes, sheets, tube bundles, corrugated sheets, honeycombs, molded parts, corona discharge points, charged plates, charged wires, and combinations thereof.

86. The filter of claim 82, wherein the filter is an electret.

87. The filter of claim 86, wherein the electret is selected from the group consisting of plastic, polypropylene, polycarbonate, FEP Teflon, poylvinylidenefluoride, $PVF_2$, and combinations thereof.

88. The filter of claim 82, further comprising an insert for receiving the filter.

89. The filter of claim 88, wherein the insert is selected from the group consisting of non-electrostatic filters, screens, wires, fibers, open cell foams, baffles, honeycombs, and combinations thereof.

90. The filter of claim 82, wherein the filter is replaceable and removably disposed.

91. The filter of claim 82, further comprising a module for the filter.

92. The filter of claim 91, wherein the module is replaceable and removably disposed on the eyewear.

93. The filter of claim 91, wherein the module is of material selected from a group consisting of molded plastic, metal, rubber, and combinations thereof.

94. The filter of claim 91, wherein the filter is removably incorporated in the module.

* * * * *